United States Patent [19]

Katsube et al.

[11] 4,217,349
[45] Aug. 12, 1980

[54] BENZISOXAZOLE DERIVATIVES

[75] Inventors: Junki Katsube, Toyonaka; Tsuyoshi Kobayashi, Niigata; Katsumi Tamoto; Yoshiaki Takebayashi, both of Takarazuka; Kikuo Sasajima, Toyonaka; Shigeho Inaba, Takarazuka; Hisao Yamamoto, Kobe, all of Japan

[73] Assignee: Sumitomo Chemical Company, Limited, Osaka, Japan

[21] Appl. No.: 919,221

[22] Filed: Jun. 26, 1978

Related U.S. Application Data

[60] Division of Ser. No. 755,139, Dec. 29, 1976, Pat. No. 4,122,176, which is a continuation-in-part of Ser. No. 590,149, Jun. 25, 1975, abandoned.

[30] Foreign Application Priority Data

Jul. 1, 1974 [JP] Japan ................................. 49-75544
Jul. 31, 1974 [JP] Japan ................................. 49-88556

[51] Int. Cl.² .................. A61K 31/535; C07D 413/06
[52] U.S. Cl. ............................. 424/248.4; 424/248.57; 424/272; 544/137; 546/198; 548/242
[58] Field of Search ............................... 544/368, 137; 260/307 DA; 546/198; 424/272, 248.4, 267, 248.57

[56] References Cited

U.S. PATENT DOCUMENTS 4,122,176 10/1978 Katsube et al. ...................... 544/368

*Primary Examiner*—Jose Tovar
*Attorney, Agent, or Firm*—Birch, Stewart, Kolasch and Birch

[57] ABSTRACT

Novel benzisoxazole compounds of the formula:

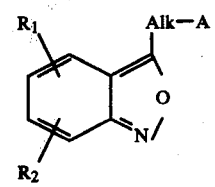

wherein $R_1$ and $R_2$ are each hydrogen, $C_1$–$C_4$ alkyl, $C_1$–$C_4$ alkoxy, ar($C_1$–$C_3$)alkoxy or halogen or, when taken together, they form $C_1$–$C_2$ alkylenedioxy, Alk is $C_1$–$C_4$ alkylene and A is a group of the formula:

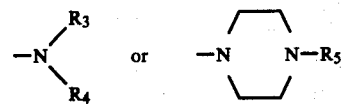

(wherein $R_3$ and $R_4$ are each $C_1$–$C_4$ alkyl or, when taken together with the adjacent nitrogen atom, they represent a 5–6 membered nitrogen-containing heterocyclic ring which may contain any additional hetero atom and $R_5$ is $C_1$–$C_4$ alkyl or aryl), and non-toxic salts thereof, which possess various pharmaceutical activities.

8 Claims, No Drawings

BENZISOXAZOLE DERIVATIVES

This application is a divisional of copending application Ser. No. 755,139 filed on Dec. 29, 1976, now U.S. Pat. No. 4,122,176 issued Oct. 24, 1978, which in turn is a continuation-in-part of application Ser. No. 590,149, filed on June 25, 1975, now abandoned.

The present invention relates to novel benzisoxazole derivatives and their use.

The benzisoxazole skeleton itself has been known since the end of the 19th century, but only a few chemical studies have been done on benzisoxazole derivatives, and only a few reports have appeared on the synthesis of the related compounds.

The novel benzisoxazole derivatives provided by this invention are benzisoxazole compounds of the formula:

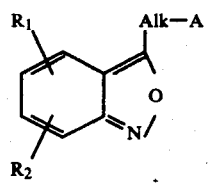

wherein $R_1$ and $R_2$ are each hydrogen, $C_1$–$C_4$ alkyl, $C_1$–$C_4$ alkoxy, ar($C_1$–$C_3$)alkoxy or halogen or, when taken together, they form $C_1$–$C_2$ alkylenedioxy, Alk is $C_1$–$C_4$ alkylene and A is a group of the formula:

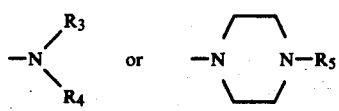

(wherein $R_3$ and $R_4$ are each $C_1$–$C_4$ alkyl or, when taken together with the adjacent nitrogen atom, they represent a 5–6 membered nitrogen-containing heterocyclic ring which may contain any additional hetero atom such as oxygen and $R_5$ is $C_1$–$C_4$ alkyl or aryl), and non-toxic salts thereof.

In the above significances, examples of "$C_1$–$C_4$ alkyl" are methyl, ethyl, n-propyl, isopropyl, n-butyl, sec.-butyl, etc., and examples of "$C_1$–$C_4$ alkoxy" are methoxy, ethoxy, n-propoxy, isopropoxy, n-butoxy, isobutoxy, t-butoxy, etc. As "halogen", there may be exemplified chlorine, bromine, fluorine, etc. Examples of "$C_1$–$C_4$ alkylene" include methylene, ethylene, propylene, butylene, methylmethylene, methylethylene and trimethylene, and examples of "$C_1$–$C_2$ alkylenedioxy" include methylenedioxy and ethylenedioxy. Examples of "aryl" include phenyl and phenyl substituted with $C_1$–$C_4$ alkyl, $C_1$–$C_4$ alkoxy or halogen and examples of "ar($C_1$–$C_3$)alkoxy" include methoxy, ethoxy and propoxy bearing aryl thereon.

As the 5–6 membered nitrogen-containing heterocyclic ring which may be represented by the symbol A, there are exemplified pyrrolidino, piperidino, morpholino, etc.

The structure of the benzisoxazole compounds [I] is characterized by the aminoalkyl side chain at the 3-position of the benzisoxazole skeleton. No reports have appeared hitherto on the synthesis of such benzisoxazole derivatives which have the aminoalkyl side chain at the 3-position of the benzisoxazole skeleton.

The benzisoxazole compounds [I] and non-toxic salts thereof exhibit significant pharmacological properties. That is, these benzisoxazole compounds all possess pharmacological activities such as central nervous system (CNS) depressing, muscle relaxing, vasodilating, bronchodilating, spasmogenic, analgesic, anti-narcotic, anti-arrhythmic, local anesthetic and/or anti-platelet aggregation activities. Therefore, these benzisoxazole derivatives may be useful as medicines such as neuroleptics, antihypertensive agents, antiasthmatic agents, spasmogens, analgesics, anti-narcotic agents, anti-arrhythmic agents, local anesthetics or anti-thrombosis agents.

Among the benzisoxazole compounds [I] of the invention, the compounds of the following formula are preferable:

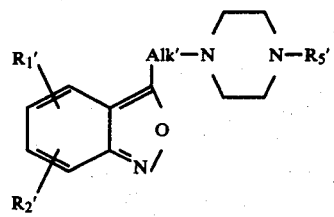

wherein $R_1'0$ and $R_2'$ are each hydrogen, $C_1$–$C_2$ alkoxy or halogen or, when taken together, they form $C_1$–$C_2$ alkylenedioxy, $R_5'$ is $C_1$–$C_2$ alkyl or aryl and Alk' is $C_2$–$C_3$ alkylene. That is, these compounds of Formula [Ia] generally show potent CNS depressing or bronchodilating activities and therefore are useful as neuroleptics or anti-asthmatic agents.

Also preferred are the compounds of the formula:

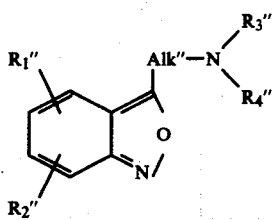

wherein $R_1''$ and $R_2''$ are each hydrogen, $C_1$–$C_2$ alkoxy or halogen or, when taken together, they form $C_1$–$C_2$ alkylenedioxy, $R_3''$ and $R_4''$ are each $C_1$–$C_4$ alkyl or, when taken together with the adjacent nitrogen atom, they represent pyrrolidino, piperidino or morpholino and Alk'' is $C_2$–$C_3$ alkylene, in view of their anti-platelet aggregation as well as CNS depressing activities. Thus, these compounds are useful as anti-thrombosis agents or neuroleptics.

Specific examples of the benzisoxazole compounds [I] are as follows:

3-(2'-Dimethylaminoethyl)-benz-2,1-isoxazole;
3-(2'-Dimethylaminoethyl)-5-methoxy-benz-2,1-isoxazole;
3-(2'-Diethylaminoethyl)-5,6-dimethoxy-benz-2,1-isoxazole;
3-(2'-Piperidinoethyl)-5,6-dimethoxy-benz-2,1-isoxazole;
3-(2'-Morpholinoethyl)-5,6-dimethoxy-benz-2,1-isoxazole;

3-(3'-Dimethylaminopropyl)-5,6-dimethoxy-benz-2,1-isoxazole;
3-(2'-Piperidinoethyl)-5,6-methylenedioxy-benz-2,1-isoxazole;
3-(2'-Diethylaminoethyl)-5,6-methylenedioxy-benz-2,1-isoxazole;
3-(2'-Morpholinoethyl)-5,6-methylenedioxy-benz-2,1-isoxazole;
3-(2'-Morpholinoethyl)-benz-2,1-isoxazole;
3-(2'-Piperidinoethyl)-benz-2,1-isoxazole;
3-(2'-Pyrrolidinoethyl)-benz-2,1-isoxazole;
3-(2'-Morpholinoethyl)-5-methoxy-benz-2,1-isoxazole;
3-(2'-Di-n-propylaminoethyl)-5-methoxy-benz-2,1-isoxazole;
3-(2'-Dimethylaminoethyl)-5-ethoxy-benz-2,1-isoxazole;
3-(2'-Dimethylaminoethyl)-6-fluoro-benz-2,1-isoxazole;
3-(2'-Morpholinoethyl)-6-fluoro-benz-2,1-isoxazole oxalate;
3-(2'-Dimethylaminoethyl)-6-methoxy-benz-2,1-isoxazole;
3-(2'-Morpholinoethyl)-6-methoxy-benz-2,1-isoxazole;
3-(1'-Diethylaminomethyl)-benz-2,1-isoxazole;
3-(2'-Morpholinoethyl)-6-chloro-benz-2,1-isoxazole;
3-(2'-Dimethylaminoethyl)-5-methyl-benz-2,1-isoxazole;
3-(2'-Dimethylaminoethyl)-6-methyl-benz-2,1-isoxazole;
3-[2'-(4''-Methylpiperazino)ethyl]-benz-2,1-isoxazole;
3-[2'-(4''-Phenylpiperazino)ethyl]-benz-2,1-isoxazole;
3-[3'-(4''-Phenylpiperazino)propyl]-benz-2,1-isoxazole;
3-[1'-(4''-Phenylpiperazino)methyl]-benz-2,1-isoxazole;
3-[2'-(4''-Phenylpiperazino)ethyl]-6-methyl-benz-2,1-isoxazole;
3-[2'-(4''-Phenylpiperazino)ethyl]-5-methoxy-benz-2,1-isoxazole;
3-[2'-(4''-Phenylpiperazino)ethyl]-6-methoxy-benz-2,1-isoxazole;
3-[2'-(4''-PHenylpiperazino)ethyl]-5,6-dimethoxy-benz-2,1-isoxazole;
3-[2'-(4''-Methylpiperazino)ethyl]-5,6-dimethoxy-benz-2,1-isoxazole;
3-[2'-(4''-o-Methoxyphenylpiperazino)ethyl]-5,6-dimethoxy-benz-2,1-isoxazole;
3-[2'-(4''-Phenylpiperazino)ethyl]-5-benzyloxy-benz-2,1-isoxazole;
3-[2'-(4''-Phenylpiperazino)ethyl]-6-fluoro-benz-2,1-isoxazole;
3-[3'-(4''-o-Methoxyphenylpiperazino)propyl]-6-fluoro-benz-2,1-isoxazole;
3-[2'-(4''-Phenylpiperazino)ethyl]-6-chloro-benz-2,1-isoxazole;
3-[2'-(4''-Phenylpiperazino)ethyl]-5,6-methylenedioxy-benz-2,1-isoxazole, etc.

The benzisoxazole componds [I] can form acid addition salts, of which examples are the hydrochloride, hydrobromide, acetate, oxalate, citrate, tartrate, succinate, fumarate, lactate, etc.

The benzisoxazole compounds [I] and their nontoxic pharmaceutically acceptable salts can be administered orally or parenterally at a dosage of generally 25–1000 mg/human body and particularly in the case of the compounds [Ia] and [Ib], a dosage of 25–500 mg/human body (about 60 kg of body weight/day) is preferred in the form of conventional pharmaceutical preparations. For instance, they can be administered in the form of conventional solid pharmaceutical preparations such as tablets or capsules, or in the form of conventional liquid pharmaceutical preparations such as suspensions, emulsions or solutions.

Besides, the benzisoxazole compounds [I] are also useful as intermediates for the preparation of other compounds which are per se useful as medicines.

The benzisoxazole compounds [I] of the invention can be prepared from the corresponding o-substituted nitrobenzenes of the formula:

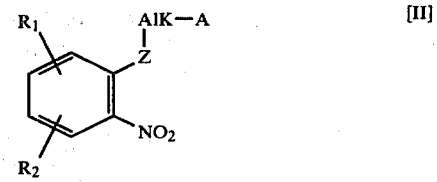

wherein Z is >CO or >CHCOR$_6$ (wherein R$_6$ is C$_{1-4}$ alkyl) and R$_2$, R$_2$, Alk and A are each as defined above by subjecting the latter to cyclization.

The cyclization may be accomplished by various procedures. As a typical example of such procedures, the o-substituted nitrobenzene of Formula [II] wherein Z is >CHCOR$_6$ may be cyclized by treatment with a base or an acid to give the benzisoxazole compound [I].

As the base, the use of a strong base such as potassium hydroxide, sodium hydroxide, potassium t-butoxide, sodium ethoxide, sodium methoxide, lithium triphenylmethane, sodium triphenylmethane or sodium hydride is preferred. As the acid, there may be employed any one having a dehydrating activity such as conc. sulfuric acid or polyphosphoric acid.

The treatment is usually carried out in the presence of an inert solvent. Examples of the inert solvent are alcohols (e.g. t-butanol, ethanol, methanol), ethers (e.g. ethyl ether, tetrahydrofuran, dioxane, dimethoxyethane), hydrocarbons (e.g. heptane, hexane, benzene, toluene), amides (e.g. dimethylformamides, hexamethylenephosphorotriamide), water, etc. The conditions, under which the treatment is made, such as temperature and time may vary depending upon the starting o-substituted nitrobenzene [II] and the base or the acid to be used therein. The treatment may be effected while warming or cooling depending upon the extent of the progress, but the temperature is usually from about −20° to 100° C. The base may be used in a stoichiometric amount or more, while the acid may be preferably employed in an excess amount so as to use the same as the medium.

Another typical example is treatment of the o-substituted nitrobenzene of the formula [II] wherein Z is >CO in any appropriate reduction system, whereby reductive cyclization takes place to give the benzisoxazole compound [I].

The reduction system may be the one using a reducing agent such as the combination of a metal or its compound (e.g. tin, zinc, stannous chloride) with an acid (e.g. hydrochloric acid, acetic acid), the combination of an alkali metal (e.g. sodium, lithium, potassium, amalgamated sodium) with an alcohol or liquid ammonia, a sulfide compound (e.g. sodium sulfide, ammonium sulfide) or the like.

Among them, one of the most preferred reducing agents is the combination of a metal or its compound with an acid. The treatment with this particular reducing agent may be carried out in the presence or absence of an inert solvent such as water, alcohols (e.g. methanol, ethanol), hydrocarbons (e.g. benzene, toluene) or ethers (e.g. ethyl ether, tetrahydrofuran, dioxane). An excess amount of the acid may be also used as a solvent. The temperature for the treatment may be varied from −20° C. to the refluxing temperature of the reduction system. Likewise, the treatment using any other reducing agent may be effected in a per se conventional manner established with regard to such reducing agent.

The reduction system may also constitute catalytic reduction, i.e. one using a hydrogenation catalyst. In this case, conventional standard procedures are applicable, but it is recommendable to use mild conditions in order to avoid overreduction. Thus, a temperature around room temperature, an atmospheric pressure of hydrogen gas and a relatively mild catalyst such as Pd-BaSO$_4$, Pd-BaCO$_3$ or a metallic catalyst poisoned with quinoline, dimethylsulfide, diethylsulfide or the like may be preferably used.

The benzisoxazole compounds [I] thus produced may be separated from the reaction mixture and purified by conventional procedures.

The thus obtained benzisoxazole compounds [I] may be converted into their addition salts in the usual manner, and reconversion from the addition salts to the original free bases may be also carried out in a conventional manner.

The following examples are given for the purpose of illustration only and are not intended to limit the invention.

EXAMPLE 1

To a mixture of 36 ml of t-butanol and 18 ml of toluene was added 1.8 g of metallic potassium, followed by heating to a solution. To this solution was added 12.6 g of 1-(2'-nitro-4',5'-dimethoxyphenyl)-1-[2'-(4''-phenylpiperazino)ethyl]propan-2-one under cooling with water, followed by stirring for 4 hours at room temperature.

The reaction mixture was poured onto ice-water and extracted with chloroform. The chloroform layer was washed with water, dried and evaporated to dryness. The oily residue was dissolved in ethyl acetate and mixed with 10 g of silica gel. The whole mixture was stirred for 30 minutes and filtered to remove off the silica gel. The filtrate was concentrated to dryness, and the residue was crystallized by methanol-ether to give 7.0 g of 3-[2'-(4''-phenylpiperazino)ethyl]-5,6-dimethoxy-benz-2,1-isoxazole having a melting point of 115°–117° C.

EXAMPLE 2

To 20 ml of sulfuric acid was added 2 g of 1-(2'-nitro-4',5'-dimethoxyphenyl)-1-[2'-(4''-phenylpiperazino)ethyl]propan-2-one, followed by stirring for 4 hours at room temperature.

The reaction mixture was poured onto ice-water, neutralized with aqueous ammonia and extracted with chloroform. The chloroform layer was washed with water, dried, treated with charcoal and evaporated to dryness. The oily residue was crystallized by methanol-ether to give 3-[2'-(4''-phenylpiperazino)ethyl]-5,6-dimethoxy-benz-2,1-isoxazole. This product was identified with the compound obtained in Example 1.

EXAMPLE 3

To a solution of 9.03 g of stannous chloride dihydrate in 72 g of conc. hydrochloric acid was added a solution of 2.59 g of 1-(2'-nitrophenyl)-3-dimethylaminopropan-1-one hydrochloride in 10 g of conc. hydrochloric acid, followed by stirring for 3 hours at room temperature.

The reaction mixture was diluted with water and stirred for several minutes, basified with aqueous sodium hydroxide under cooling and extracted with chloroform. The chloroform layer was washed with water, dried and concentrated to dryness. The oily residue was dissolved in ethanol and mixed with 4.5 g of oxalic acid in ethanol. The deposited precipitates were collected and recrystallized from ethanol to give 2.2 g of 3-(2'-dimethylaminoethyl)benz-2,1-isoxazole oxalate having a melting point of 145°–146.5° C.

EXAMPLE 4

Using the procedure similar to that described in Example 3 but replacing 1-(2'-nitrophenyl)-3-dimethylaminopropan-1-one hydrochloride by 1-(2'-nitro-5'-methoxyphenyl)-3-dimethylaminopropan-1-one hydrochloride, there was obtained 3-(2'-dimethylaminoethyl)-5-methoxy-benz-2,1-isoxazole oxalate having a melting point of 159°–160° C.

EXAMPLE 5

Using the procedure similar to that described in Example 3 but replacing 1-(2'-nitrophenyl)-3-dimethylaminopropan-1-one hydrochloride by 1-(2'-nitrophenyl)-3-(4'-phenylpiperazino)propan-1-one hydrochloride, there was obtained 3-[2'-(4''-phenylpiperazino)ethyl]-benz-2,1-isoxazole oxalate having a melting point of 194°–196° C.

EXAMPLE 6

Using the procedure similar to that described in Example 3 but replacing 1-(2'-nitrophenyl)-3-dimethylaminopropan-1-one hydrochloride by 1-(2'-nitro-4'-fluorophenyl)-4-(4'-o-methoxyphenylpiperazino)butan-1-one hydrochloride and oxalic acid by hydrogen chloride, there was obtained 3-[3'-(4''-o-methoxyphenylpiperazino)propyl]-6-fluorobenz-2,1-isoxazole hydrochloride having a melting point of 191°–195° C.

EXAMPLE 7

A mixture of 0.8 g of 1-(2'-nitrophenyl)-3-dimethylaminopropan-1-one hydrochloride and 4.5 g of sodium sulfide in 45 ml of methanol was heated under reflux for 10 hours. The reaction mixture was filtered and the filtrate was concentrated to dryness. The residue was dissolved in chloroform, washed with water, dried and concentrated to dryness. The residue was chromatographed on silica gel and treated with oxalic acid to give 3-(2'-dimethylaminoethyl)-benz-2,1-isoxazole oxalate. This product was identified with the compound obtained in Example 3.

EXAMPLE 8

Using the procedure similar to that described in Example 7 but replacing 1-(2'-nitrophenyl)-3-dimethylaminopropan-1-one hydrochloride by 1-(2'-nitrophenyl)-3-(4'-phenylpiperazino)propan-1-one hydrochloride, there was obtained 3-[2'-(4''-phenylpiperazino)ethyl]-benz-2,1-isoxazole oxalate. This product was identified with the compound obtained in Example 5.

EXAMPLE 9

0.8 g of 1-(2'-nitrophenyl)-3-dimethylaminopropan-1-one hydrochloride in 12 ml of acetic acid was hydrogenated over 120 mg of 5% palladium-barium sulfate. After 2 equivalents of hydrogen was absorbed, the reaction mixture was filtered and the filtrate was concentrated to dryness. The residue was dissolved in chloroform, washed with 2% aqueous sodium hydroxide and then with water, dried and concentrated to dryness. The residue was chromatographed on silica gel and treated with oxalic acid to give 3-(2'-dimethylaminoethyl)-benz-2,1-isoxazole oxalate. This product was identified with the compound obtained in Example 3.

EXAMPLE 10

Using the procedure similar to that described in Example 9 but replacing 1-(2'-nitrophenyl)-3-dimethylaminopropan-1-one hydrochloride by 1-(2'-nitrophenyl)-3-(4'-phenylpiperazino)propan-1-one hydrochloride, there was obtained 3-[2'-(4''-phenylpiperazino)ethyl]-benz-2,1-isoxazole oxalte. This product was identified with the compound obtained in Example 5.

The following compounds were produced in a manner similar to that in Examples 1 and 3.

3-(2'-Diethylaminoethyl)-5,6-dimethoxy-benz-2,1-isoxazole oxalate, m.p. 160°–162° C.;

3-(2'-Piperidinoethyl)-5,6-dimethoxy-benz-2,1-isoxazole oxalate, m.p. 199°–200° C.;

3-(2'-Morpholinoethyl)-5,6-dimethoxy-benz-2,1-isoxazole oxalate, m.p. 183°–185° C.;

3-(3'-Dimethylaminopropyl)-5,6-dimethoxy-benz-2,1-isoxazole oxalate, m.p. 145°–147° C.;

3-[2'-(4''-Phenylpiperazino)ethyl]-5,6-methylenedioxy-benz-2,1-isoxazole, m.p. 126°–127.5° C.;

3-(2'-Piperidinoethyl)-5,6-methylenedioxy-benz-2,1-isoxazole, m.p. 97.5°–99.5° C.;

3-(2'-Diethylaminoethyl)-5,6-methylenedioxy-benz-2,1-isoxazole oxalate, m.p. 168.5°–169.5° C.;

3-(2'-Morpholinoethyl)-5,6-methylenedioxy-benz-2,1-isoxazole, m.p. 116.5°–119° C.;

3-[2'-(4''-Phenylpiperazino)ethyl]-benz-2,1-isoxazole oxalate, m.p. 194°–196° C.;

3-(2'-Morpholinoethyl)-benz-2,1-isoxazole oxalate, m.p. 174°–175° C.;

3-(2'-Piperidinoethyl)-benz-2,1-isoxazole oxalate, m.p. 154°–155° C.;

3-(2'-Pyrrolidinoethyl)-benz-2,1-isoxazole oxalate, m.p. 152°–153° C.;

3-[2'-(4''-Methylpiperazino)ethyl]-benz-2,1-isoxazole oxalate, m.p. 229°–232° C.;

3-(2'-Morpholinoethyl)-5-methoxy-benz-2,1-isoxazole oxalate, m.p. 178°–180° C.;

3-(2'-Di-n-propylaminoethyl)-5-methoxy-benz-2,1-isoxazole oxalate, m.p. 146°–148° C.;

3-(2'-Dimethylaminoethyl)-5-ethoxy-benz-2,1-isoxazole oxalate, m.p. 153°–155° C.;

3-(2'-Dimethylaminoethyl)-6-fluoro-benz-2,1-isoxazole oxalate, m.p. 150°–151° C.;

3-(2'-Morpholinoethyl)-6-fluoro-benz-2,1-isoxazole oxalate, m.p. 176°–177° C.;

3-(2'-Dimethylaminoethyl)-6-methoxy-benz-2,1-isoxazole oxalate, m.p. 172°–174° C.;

3-(2'-Morpholinoethyl)-6-methoxy-benz-2,1-isoxazole oxalate, m.p. 147°–148° C.

What is claimed is:

1. A compound of the formula:

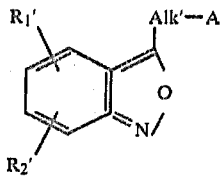

wherein $R_1'$ and $R_2'$ are each hydrogen, $C_1$–$C_4$ alkyl, $C_1$–$C_4$ alkoxy, ar($C_1$–$C_3$) alkoxy or halogen or, when taken together, $R_1'$ and $R_2'$ form $C_1$–$C_2$ alkylenedioxy, Alk' is $C_1$–$C_4$ alkylene and A is a group of the formula:

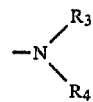

wherein $R_3$ and $R_4$ are each $C_1$–$C_4$ alkyl or, when taken together with the adjacent nitrogen atom, $R_3$ and $R_4$ form a pyrrolidino, piperidino or morpholino ring.

2. A compound of the formula:

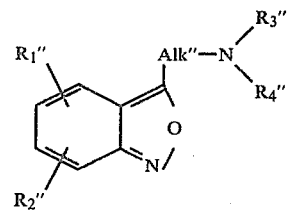

wherein $R_1''$ and $R_2''$ are each hydrogen, $C_1$–$C_2$ alkoxy or halogen or, when taken together, they form $C_1$–$C_2$ alkylenedioxy, $R_3''$ and $R_4''$ are each $C_1$–$C_4$ alkyl or, when taken together with the adjacent nitrogen atom, they represent pyrrolidino, piperidino or morpholino and Alk'' is $C_2$–$C_3$ alkylene, or a non-toxic salt thereof.

3. 3-(2'-Dimethylaminoethyl)-5-methoxy-benz-2,1-isoxazole or a non-toxic salt thereof.

4. 3-(2'-Dimethylaminoethyl)-6-fluoro-benz-2,1-isoxazole or a non-toxic salt thereof.

5. A pharmaceutical composition consisting essentially of an effective central nervous system depressing or anti-platelet aggregation amount of the compound of claim 2, and at least one pharmaceutically acceptable inert carrier or diluent.

6. A method of inducing a central nervous system depressing or anti-platelet aggregation effect in animals or human beings, which comprises administering thereto an amount of the compound of claim 2 effective to induce said effect.

7. A pharmaceutical composition consisting essentially of an effective central nervous system depressing, muscle relaxing, vasodilating, bronchodilating, spasmogenic, analgesic, anti-narcotic, anti-arrhythmic, local anesthetic or anti-platelet aggregation amount of the compound of claim 1, and at least one pharmaceutically acceptable inert carrier or diluent.

8. A method for inducing a central nervous system depressing, muscle relaxing, vasodilating, bronchodilating, spasmogenic, analgesic, anti-narcotic, anti-arrhythmic, local anesthetic or anti-platelet aggregation effect in animals or human beings, which comprises administering thereto an amount of the compound of claim 1, effective to induce said effect.

* * * * *